United States Patent
Keady et al.

(10) Patent No.: US 9,653,260 B2
(45) Date of Patent: May 16, 2017

(54) HIGH THROUGHPUT TEM PREPARATION PROCESSES AND HARDWARE FOR BACKSIDE THINNING OF CROSS-SECTIONAL VIEW LAMELLA

(71) Applicant: FEI Company, Hillsboro, OR (US)

(72) Inventors: Paul Keady, Portland, OR (US); Brennan Peterson, Portland, OR (US); Guus Das, Valkenswaard (NL); Craig Henry, Hillsboro, OR (US); Larry Dworkin, Portland, OR (US); Jeff Blackwood, Portland, OR (US); Stacey Stone, Beaverton, OR (US); Michael Schmidt, Gresham, OR (US)

(73) Assignee: FEI Company, Hillsboro, OR (US)

( * ) Notice: Subject to any disclaimer, the term of this patent is extended or adjusted under 35 U.S.C. 154(b) by 881 days.

(21) Appl. No.: 13/691,270

(22) Filed: Nov. 30, 2012

(65) Prior Publication Data
US 2013/0248354 A1    Sep. 26, 2013

Related U.S. Application Data

(60) Provisional application No. 61/565,506, filed on Dec. 1, 2011, provisional application No. 61/569,089, filed on Dec. 9, 2011.

(51) Int. Cl.
*G01N 1/32* (2006.01)
*H01J 37/305* (2006.01)
(Continued)

(52) U.S. Cl.
CPC ...... *H01J 37/3056* (2013.01); *C23C 14/5833* (2013.01); *G01N 1/32* (2013.01);
(Continued)

(58) Field of Classification Search
CPC .................. C23C 14/5833; H01J 37/26
See application file for complete search history.

(56) References Cited

U.S. PATENT DOCUMENTS

| | | | |
|---|---|---|---|
| 5,435,850 | A | 7/1995 | Rasmussen |
| 5,851,413 | A | 12/1998 | Casella et al. |

(Continued)

FOREIGN PATENT DOCUMENTS

| | | |
|---|---|---|
| JP | 2000-214056 | 8/2000 |
| JP | 2007303946 A | 11/2007 |

(Continued)

OTHER PUBLICATIONS

Hartfield, C. et al., "Sample Repositioning Solutions for in situ Preparation and Analysis" 2010 DC Area FIB User's Group, Feb. 25, 2010, 23 pages.

*Primary Examiner* — Jason M Berman
(74) *Attorney, Agent, or Firm* — Scheinberg & Associates, P.C.; John B. Kelly

(57) ABSTRACT

A method for TEM sample preparation and analysis that can be used in a FIB-SEM system without re-welds, unloads, user handling of the lamella, or a motorized flip stage. The method allows a dual beam FIB-SEM system with a typical tilt stage to be used to extract a sample to from a substrate, mount the sample onto a TEM sample holder capable of tilting, thin the sample using FIB milling, and rotate the sample so that the sample face is perpendicular to an electron column for STEM imaging.

26 Claims, 10 Drawing Sheets

(51) Int. Cl.
*C23C 14/58* (2006.01)
*H01J 37/28* (2006.01)
*H01J 37/30* (2006.01)

(52) U.S. Cl.
CPC .......... *H01J 37/28* (2013.01); *H01J 37/3005* (2013.01); *H01J 2237/31745* (2013.01); *H01J 2237/31749* (2013.01)

(56) References Cited

U.S. PATENT DOCUMENTS

| | | | |
|---|---|---|---|
| 6,538,254 B1 * | 3/2003 | Tomimatsu | H01J 37/3056 250/442.11 |
| 6,768,110 B2 | 7/2004 | Alani | |
| 6,914,244 B2 | 7/2005 | Alani | |
| 7,423,263 B2 * | 9/2008 | Hong | G01N 1/32 250/304 |
| 7,474,419 B2 | 1/2009 | Tappel et al. | |
| 8,134,124 B2 | 3/2012 | Blackwood et al. | |
| 8,525,137 B2 | 9/2013 | Blackwood et al. | |
| 8,766,214 B2 | 7/2014 | Routh, Jr. et al. | |
| 8,822,913 B2 | 9/2014 | Graupera et al. | |
| 8,835,845 B2 | 9/2014 | Hong | |
| 8,859,963 B2 | 10/2014 | Moriarty et al. | |
| 8,859,998 B2 | 10/2014 | Blackwood et al. | |
| 2004/0217286 A1 | 11/2004 | Alani | |
| 2006/0011868 A1 | 1/2006 | Kidron et al. | |
| 2008/0067374 A1 | 3/2008 | Ono et al. | |
| 2008/0073535 A1 | 3/2008 | Hong et al. | |
| 2008/0296498 A1 | 12/2008 | Hong | |
| 2009/0114842 A1 | 5/2009 | Takahashi et al. | |
| 2010/0211386 A1 | 8/2010 | Lee et al. | |
| 2010/0213386 A1 | 8/2010 | Man et al. | |
| 2011/0017922 A1 | 1/2011 | Amador | |
| 2012/0112064 A1 | 5/2012 | Nagakubo et al. | |
| 2012/0298884 A1 | 11/2012 | Nakajima et al. | |
| 2013/0319849 A1 | 12/2013 | Fuller et al. | |
| 2013/0328246 A1 | 12/2013 | Wells et al. | |

FOREIGN PATENT DOCUMENTS

| | | |
|---|---|---|
| JP | 2008026312 A | 2/2008 |
| JP | 2009014709 A | 1/2009 |
| JP | 2009110745 A | 5/2009 |
| JP | 2010109808 A | 9/2010 |
| WO | 2011093316 A1 | 8/2011 |
| WO | 2014055974 A1 | 4/2014 |

* cited by examiner

HIGH THROUGHPUT TEM PREPARATION PROCESSES AND HARDWARE FOR BACKSIDE THINNING OF CROSS-SECTIONAL VIEW LAMELLA

This Application claims priority from U.S. Provisional Application No. 61/565,506, filed Dec. 1, 2011, and from U.S. Provisional Application No. 61/569,089, filed Dec. 9, 2011, both of which are hereby incorporated by reference.

TECHNICAL FIELD OF THE INVENTION

The present invention relates to preparation of samples for viewing in charged particle beam systems.

BACKGROUND OF THE INVENTION

Charged particle beam microscopy, such as scanning ion microscopy and electron microscopy, provides significantly higher resolution and greater depth of focus than optical microscopy. In a scanning electron microscope (SEM), a primary electron beam is focused to a fine spot that scans the surface to be observed. Secondary electrons are emitted from the surface as it is impacted by the primary electron beam. The secondary electrons are detected, and an image is formed, with the brightness at each point on the image being determined by the number of secondary electrons detected when the beam impacts a corresponding spot on the surface. Scanning ion microscopy (SIM) is similar to scanning electron microscopy, but an ion beam is used to scan the surface and eject the secondary electrons.

In a transmission electron microscope (TEM), a broad electron beam impacts the sample and electrons that are transmitted through the sample are focused to form an image of the sample. The sample must be sufficiently thin to allow many of the electrons in the primary beam to travel though the sample and exit on the opposite site. Samples are typically less than 100 nm thick.

In a scanning transmission electron microscope (STEM), a primary electron beam is focused to a fine spot, and the spot is scanned across the sample surface. Electrons that are transmitted through the work piece are collected by an electron detector on the far side of the sample, and the intensity of each point on the image corresponds to the number of electrons collected as the primary beam impacts a corresponding point on the surface.

Because a sample must be very thin for viewing with transmission electron microscopy (whether TEM or STEM), preparation of the sample can be delicate, time consuming work. The term "TEM" sample as used herein refers to a sample for either a TEM or an STEM and references to preparing a sample for a TEM are to be understood to also include preparing a sample for viewing on an STEM.

TEM samples are typically less than 100 nm thick, but for some applications samples must be considerably thinner. Thickness variations in the sample result in sample bending, over-milling, or other catastrophic defects. For such small samples, preparation is a critical step in TEM analysis that significantly determines the quality of structural characterization and analysis of the smallest and most critical structures.

FIG. 1 shows one type of typical TEM sample holder 100 commonly called a "grid", which comprises a partly circular 3 mm ring. In some applications, a sample 104 is attached to a finger 106 of the TEM grid by ion beam deposition or an adhesive. The sample extends from the finger 106 so that in a TEM (not shown) an electron beam will have a free path through the sample 104 to a detector under the sample. The TEM grid is typically mounted horizontally onto a sample holder in the TEM with the plane of the TEM grid (and thus the plane of the attached sample) perpendicular to the electron beam, and the sample is observed.

FIG. 2 shows a cross-sectional view of TEM sample 200 that is partly extracted from a substrate or work piece 202 using a typical process. An ion beam 204 cuts trenches 206 and 208 on both side of sample to be extracted, leaving a thin lamella 210 having a major surface 212 that will be observed by an electron beam. The sample 200 is then freed by tilting the work piece 202 in relation to an ion beam, and cutting around its sides and bottom. A probe 216 attaches to the top of the sample 200, before or after it is freed, and transports the sample to a TEM grid. FIG. 2 shows sample 200 almost entirely freed, remaining attached by a tab 218 on one side. FIG. 2 shows ion beam 204 ready to sever tab 218.

TEM samples can be broadly classified as "cross-sectional view" samples or "planar view" samples, depending on how the sample was oriented on the work piece. If the face of the sample to be observed was parallel to the surface of the work piece, the sample is referred to as a "planar view" or "plan view" sample. If the face to be observed was perpendicular to the work piece surface, the sample is referred to as a "cross-sectional view" sample.

FIG. 3 shows a substrate or work piece 300 from which a cross-sectional view sample 302 is being extracted. The sample 302 is undercut by two intersecting ion beam cuts 306A and 306B from opposite directions, and then the ion beam cuts the sides 308A and 308B to free a "chunk" or large sample that requires additional thinning before observation. A probe 310 is attached to the top surface of the sample 304. The extracted sample is therefore oriented horizontally. With the sample attached in a horizontal orientation to a vertically oriented TEM grid, the sample extends normal to the plane of the grid, and the top surface of the sample 304 is unobstructed for thinning from the top side with a FIB.

Thinning a TEM sample from the top side is commonly called "top down" thinning. A significant problem for the preparation of TEM samples from the top side is commonly referred to as "curtaining." Curtaining is most often observed in semiconductor materials where multiple patterned layers of materials having a low sputtering yield blocks a faster sputtering yield material. Curtaining may also be observed in materials exhibiting different topographic regions where changes in sputtering yields vary with the milling incident angle. FIB thinning of a sample having these types of structural or density variations will cause a "curtain" to propagate from the bottom of the density-variation structure (i.e. metal line) down the face of the milled cross-section. Curtaining artifacts reduce the quality of the TEM imaging and limit the minimal useful specimen thickness. For ultra-thin TEM samples, defined herein as samples having a thickness of less than 30 nm, the two cross-section faces are obviously in very close proximity so thickness variations from curtaining effects can cause a sample to be unusable.

In order to minimize curtaining in TEM sample preparation, it is known to invert the sample so that the bottom or backside of the sample (bulk silicon) is facing the FIB column Because the bulk portion of the sample will not have imbedded features such as metal lines or transistors, curtaining artifacts will not be introduced into the portion of the sample face containing the region of interest, i.e., the layers of circuitry on the top surface of the semiconductor. While this technique works reasonably well in the preparation of TEM samples, it is difficult to expose and thin the backside of a cross-sectional sample in a conventional FIB system. In systems without an expensive flipstage, often two or even three separate probe manipulations and welds are required to invert the sample without venting and unloading the vacuum. Prior art techniques and devices for accomplishing the sample inversion either require expensive additional equipment, or time-consuming additional manipulation and welding steps, or even manual sample manipulation outside vacuum.

What is needed is an improved method for TEM sample preparation including backside thinning that can be used with conventional sample stages without the use of expensive additional equipment and that can be performed more rapidly and without breaking vacuum.

SUMMARY OF THE INVENTION

An object of the invention, therefore, is to provide a backside (silicon-side) thinned cross-sectional view TEM lamella which can be created and thinned without tweezers, re-welds, or user handling of the lamella. Preferred embodiments of the present invention allow a dual beam FIB-SEM system used for lamella creation and analysis with a lift out needle oriented at some angle between 0 and 90 degrees with respect to horizontal to be used to extract a sample from a substrate, mount the sample onto a TEM sample holder, thin the sample using FIB milling, and optionally rotate the sample so that the sample face or appropriate surface is essentially perpendicular to an electron column for STEM imaging.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which.

The accompanying drawings are not intended to be drawn to scale. In the drawings, each identical or nearly identical component that is illustrated in various figures is represented by a like numeral. For purposes of clarity, not every component may be labeled in every drawing.

DETAILED DESCRIPTION OF PREFERRED EMBODIMENTS

Figure 1:
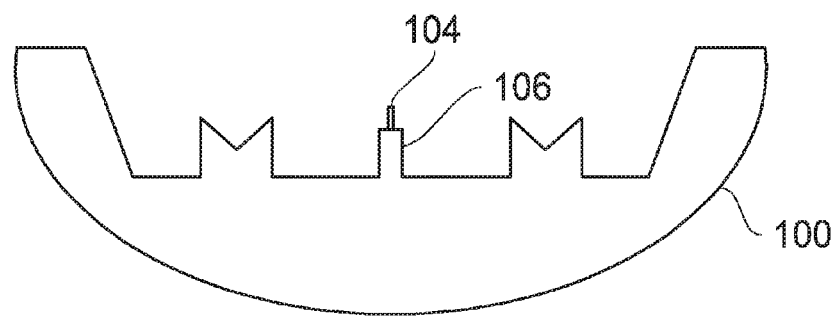
FIG. 1 shows a typical TEM sample holder comprising a partly circular ring.

Preferred embodiments of the present invention provide an improved method for TEM/STEM sample creation and thinning that can be performed within a FIB-SEM dual beam system preferably without unloading or user handling of the lamella, grid, or other small/delicate objects. Conventional lamella creation and preparation can take upwards of several hours per sample. Significantly higher throughput and process robustness is realized with preferred embodiments of the present invention by dramatically reducing the preparation time without the need to re-weld the sample, unload the sample from the vacuum chamber, and manually handle the sample.

Preferred embodiments of the present invention are directed at a novel method of preparing backside thinned cross-sectional TEM samples. Preferred embodiments of the present invention combine a lift-out probe needle rotation technique with a TEM sample holder capable of tilting and mounted onto a stage capable of moving in the X, Y, and Z directions and capable of tilting and rotating. By utilizing this combination, samples can be mounted to the grid such that the backside of the sample is exposed to the FIB for thinning while preferably being imaged with the SEM. Once the sample is prepared, it can be analyzed by STEM or TEM. Preferred embodiments of the present invention are performed within the dual beam FIB-SEM system.

A preferred method or apparatus of the present invention has many novel aspects, and because the invention can be embodied in different methods or apparatuses for different purposes, not every aspect need be present in every embodiment. Moreover, many of the aspects of the described embodiments may be separately patentable.

A preferred method of preparing a sample for TEM imaging according to the present invention comprises the following steps:

providing a substrate inside a dual beam FIB-SEM system, and said system comprising a SEM column and a FIB column oriented at an angle relative to the SEM column;

providing a lift-out needle or probe for manipulating a freed sample, said lift-out needle or probe oriented at an angle relative to the SEM column and capable of rotation about its axis;

providing a sample holder for holding an extracted TEM/STEM sample, the sample holder mounted on a sample stage inside the FIB-SEM system, said sample stage having a sample stage plane and comprising a rotating and tilting stage, and said sample holder comprising a tilting sample holder ;

freeing a sample from the substrate using an ion beam, said freed sample having a top surface and a backside surface;

extracting the freed sample from the substrate with the lift-out needle or probe;

rotating the lift-out needle or probe by 180 degrees, changing the orientation of the top surface of the freed sample from a horizontal position to a transposed position pre-tilting the sample holder to a first angle;

mounting the sample onto the pre-tilted sample holder so that the top surface of the sample is perpendicular to the sample holder plane;

tilting the sample holder so that the sample holder is oriented vertically with respect to the plane of the stage;

tilting the sample stage to a second angle such that the top surface of the mounted sample being oriented essentially perpendicular to the orientation of the FIB column, having the backside surface exposed to the FIB column;

thinning a first side of the sample using the ion beam by milling the sample from the backside, said milling producing a sample face perpendicular to the orientation of the FIB column;

compucentrically rotating the stage 180 degrees;

thinning a second side of the sample using the ion beam by milling the sample from the backside, said milling producing an opposite sample face substantially perpendicular to the orientation of the FIB column;

optionally tilting the sample holder to third angle, such that the sample face is oriented substantially perpendicular to the vertical SEM column; and optionally viewing the mounted sample with the TEM.

Figure 4A:
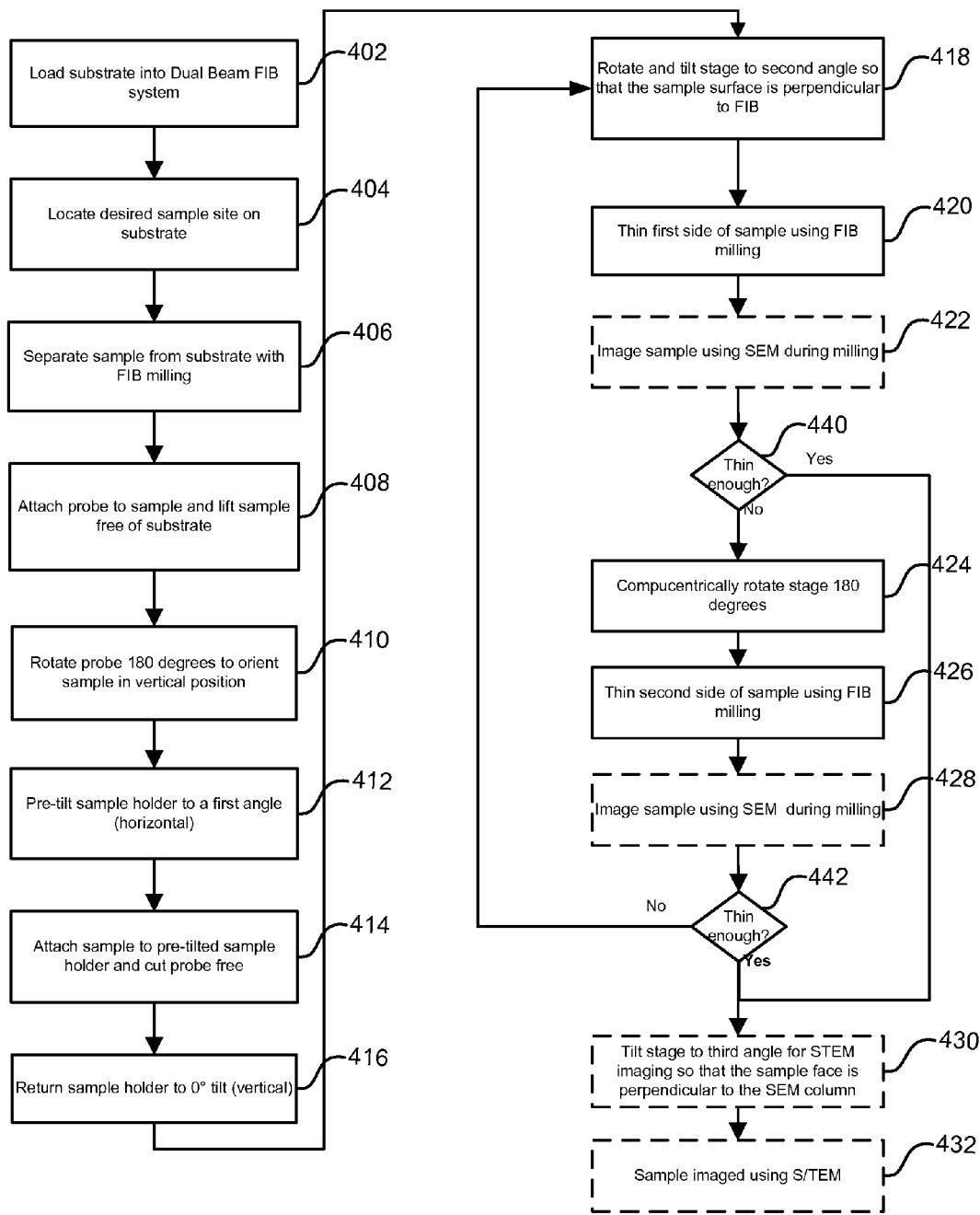
FIG. 4A is a flowchart showing the steps of creating and imaging of a backside thinned cross-sectional sample according to a preferred embodiment of the present invention.

FIG. 4A is a flowchart showing the steps of creating and imaging of a backside thinned cross-sectional sample according to a preferred embodiment of the present invention. Various steps in the process are shown in FIGS. 5A-5G.

First, in step 402, a substrate such as a semiconductor wafer or portion thereof is loaded into a dual beam FIB-SEM system having both a FIB column and a SEM column A typical dual-beam configuration has an electron column having a vertical axis with an ion column having an axis tilted with respect to the vertical (usually at a tilt of approximately 52 degrees). The substrate can be auto-loaded, as is well known in the art, although the substrate can also be loaded manually. The steps of this process are preferably performed within the dual-beam system.

In step 404, the location of a sample (containing a feature of interest) to be extracted from a substrate is determined For example, the substrate may be a semiconductor wafer or portion thereof and the portion to be extracted may include a portion of an integrated circuit that is to be observed using the TEM. The dual beam system's imaging capabilities can be used to visually select the area which contains the feature of interest. The system's navigation capabilities can also be used to select the area of interest by providing coordinates to the system which are mapped to the substrate and having the system navigate to those coordinates.

Figure 2:
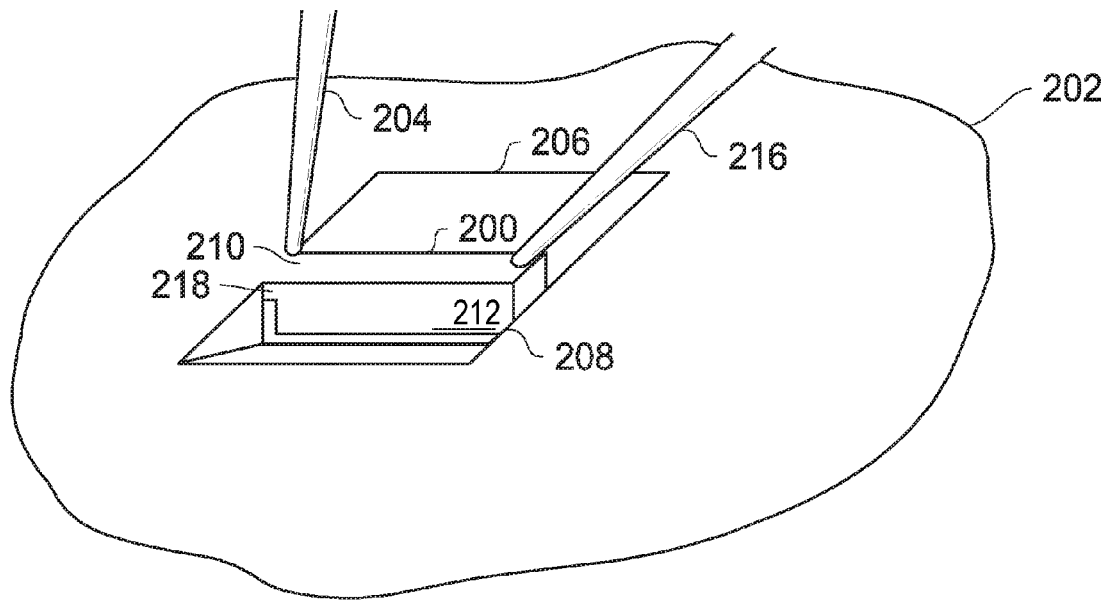
FIG. 2 shows a cross-sectional view of a TEM sample partly extracted from a substrate using a typical process.
Figure 3:
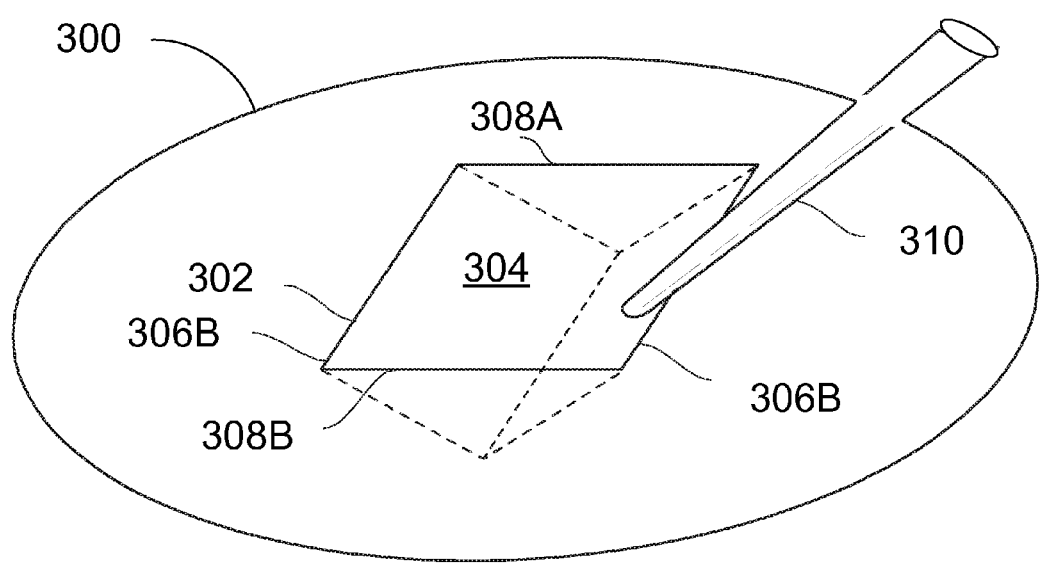
FIG. 3 shows a planar view sample being extracted from a substrate using a typical process.
Figure 5A:
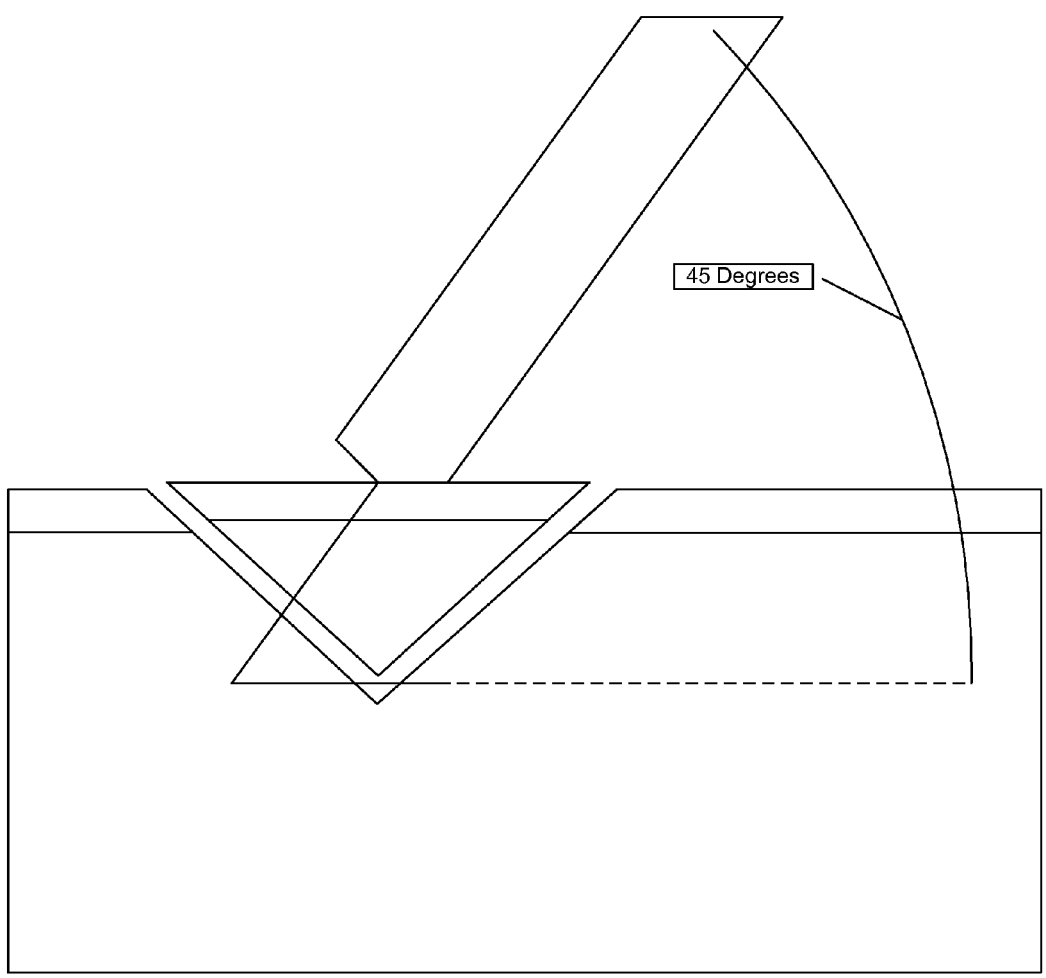
FIG. 5A is a schematic cross-sectional view of a lift-out probe needle attached to a sample freed from the substrate.

In step 406, the sample is separated from the substrate by milling with a focused ion beam as described above and shown in FIGS. 2-3. Next, in step 408, a lift-out probe tip is attached to the sample by FIB-induced chemical vapor deposition and the sample is lifted free of the substrate as shown in FIG. 5A. The probe is oriented at an angle of 45 degrees relative to the surface of the sample. The probe can be attached to the sample, for example, by static electricity, FIB deposition, or an adhesive. Steps 406 and 408 are preferably carried out with the FIB-SEM sample stage at a tilt of zero degrees (so that the sample stage plane is perpendicular to the vertical).

Figure 5B:
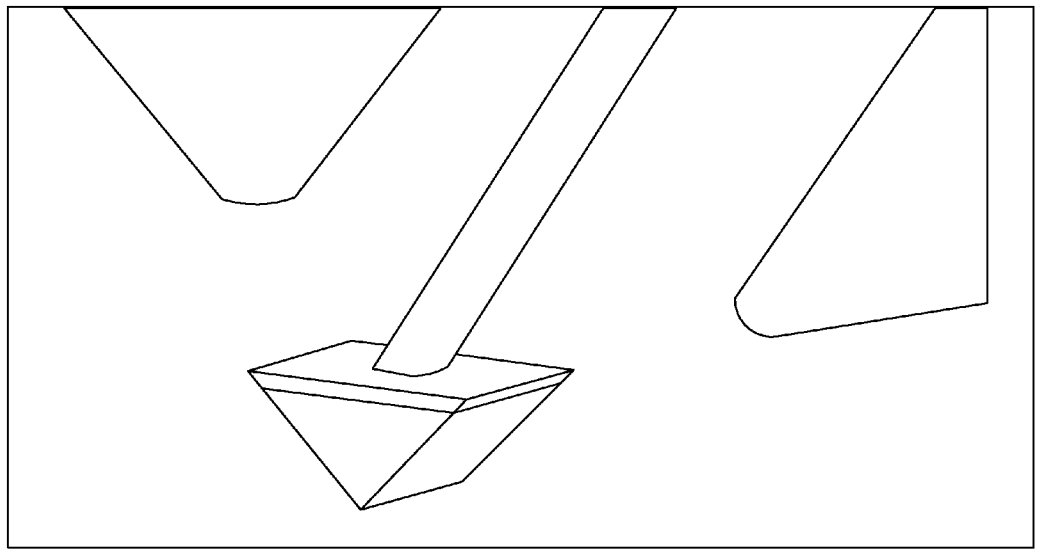
FIG. 5B is a schematic view of a lift-out probe needle attached to a sample where the needle is at an angle relative to the surface of the sample.
Figure 5C:
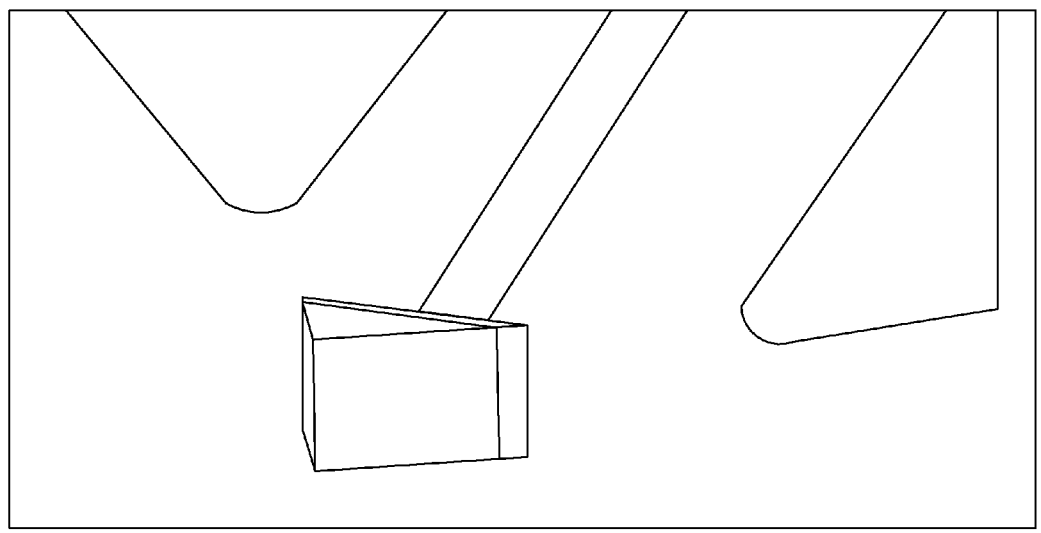
FIG. 5C is a schematic view of the sample in FIG. 5B after the needle is rotated 180 degrees about its axis.

In step 410, the lift-out probe needle is rotated 180 degrees, changing the orientation of the sample from a horizontal position shown in FIG. 5B to a transposed upright position shown in FIG. 5C. For example, with the lift-out probe attached when oriented at 45 degrees relative to the sample (horizontal plane), rotating the lift-out needle 180 degrees about the longitudinal axis of the needle, will transpose the sample surface into a vertical position of 90 degrees relative to the horizontal plane.

The TEM sample holder is preferably mounted vertically onto a stage so that the vertical axis of the TEM sample holder is perpendicular to the plane of the sample stage surface. In step 412, the TEM sample holder is pre-tilted to a first angle of 90 degrees to a horizontal orientation as shown in FIG. 5D.

Figure 5D:
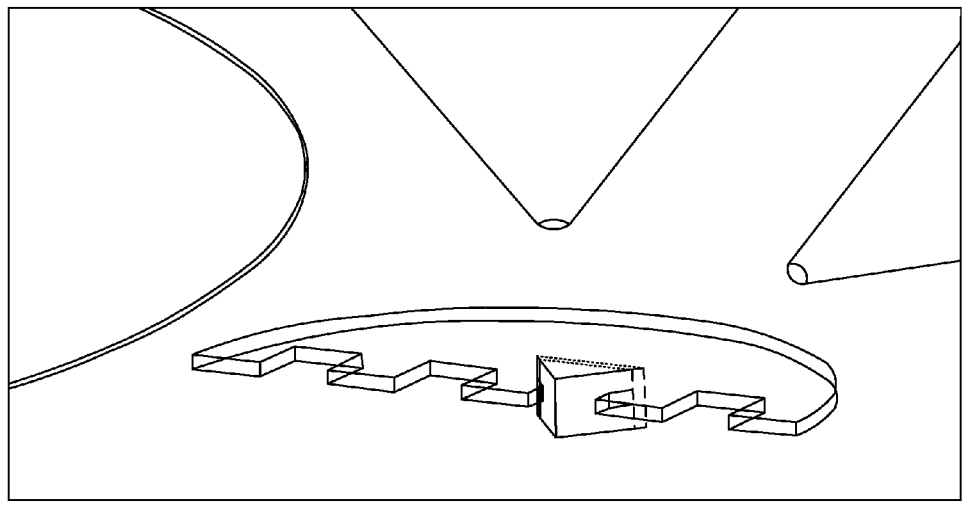
FIG. 5D is a schematic view of the sample in FIG. 5C after it is attached to the sample holder grid.

In step 414, the rotated sample of FIG. 5C is attached to the horizontal grid, typically by chemical vapor deposition or an adhesive, and the attached probe is cut free as shown in FIG. 5D. The rotated sample is attached to the sample holder so that the top surface of the sample is perpendicular to the grid (FIG. 5D).

Figure 5E:
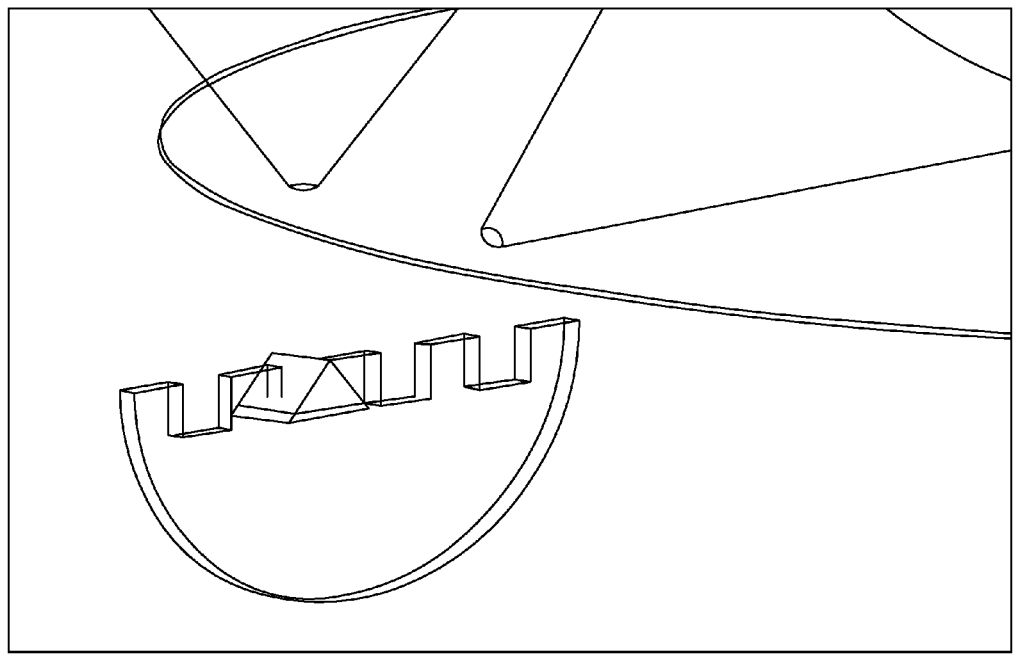
FIG. 5E is a schematic view of the sample holder grid returned to the neutral position.
Figure 5F:
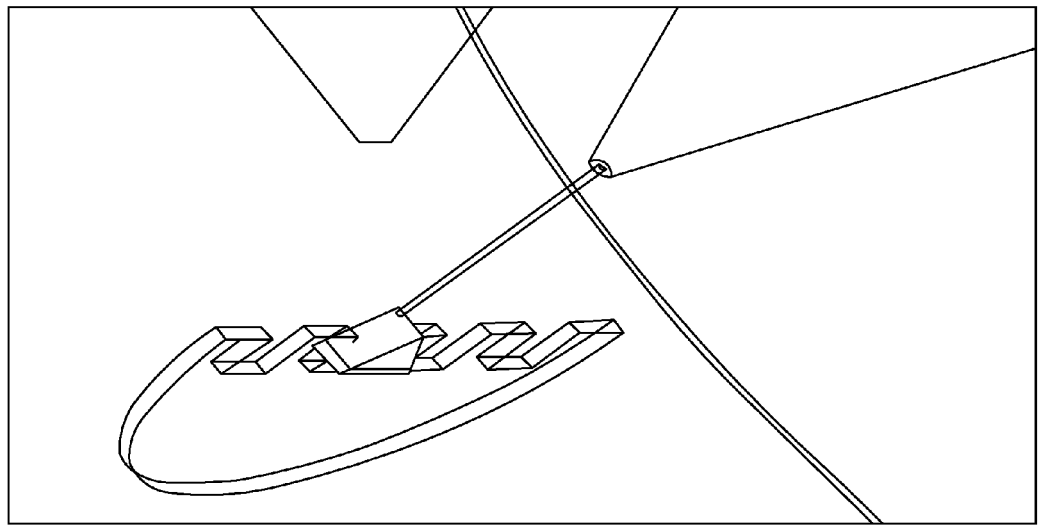
FIG. 5F is a schematic view of the sample rotated and tilted so that the first side of the sample can be milled

In step 416, the sample holder is returned to zero degree tilt as shown in FIG. 5E. In step 418, shown in FIG. 5F, the stage is rotated and then tilted to a second angle such that the top surface of the mounted sample is preferably oriented perpendicular to the orientation of the FIB column, preferably having the backside surface exposed to the FIB column In step 420, the first side of sample is thinned using FIB milling as shown in FIG. 5F. Milling from the backside is preferred and minimizes or prevents curtaining. In step 422, the first side of the sample is preferably imaged using an SEM or STEM during the milling of the sample.

Figure 5G:
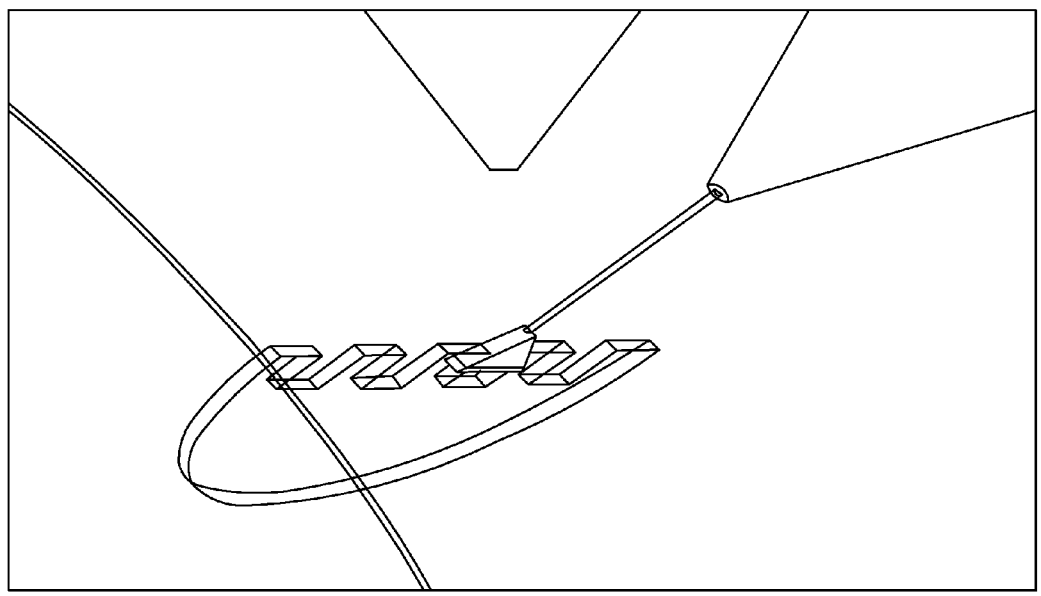
FIG. 5G is a schematic view of the sample rotated and tilted so that the second side of the sample can be milled

Once the first side of the sample is thinned, in step 424 the sample is preferably compucentrically or eucentrically rotated 180 degrees so that the second side of the sample can be thinned. The sample holder is tilted to a vertical position of 90 degrees relative to the stage and the stage is then rotated 180 degrees. Other methods of rotation and re-orientation of the sample are possible in which the second side of the sample is positioned for thinning Next, the stage is tilted to the second angle such that the top surface of the mounted sample is preferably oriented substantially perpendicular to the orientation of the FIB column, preferably having the backside surface exposed to the FIB column as shown in FIG. 5G. The second angle of tilt preferably allows for an orthogonal face surface to be formed.

In step 426, the second side of the sample is thinned using FIB milling as shown in FIG. 5G. Milling from the backside is preferred and minimizes or prevents curtaining. In step 428, the second side of the sample is preferably imaged using an SEM during the milling of the sample.

Steps 418 through 428 can be repeated as needed to thin the sample to a desired thickness or until a feature of the sample is visible or available for imaging. In decision block 440, if the sample is thinned to the desired thickness or feature and no further thinning is required, then the process proceeds to optional step 430. If the sample requires additional thinning, the process returns to step 424 and the second side of the sample is subsequently thinned. In decision block 442, if the sample is thinned to the desired thickness or feature and no further thinning is required, then the process proceeds to optional step 430. If the sample requires additional thinning, the process returns to step 418 and the first side of the sample is subsequently thinned again.

Once thinning of both sides of the sample is completed, the remaining sample is sufficiently thin for viewing with transmission electron microscopy. Optionally in step 430, the sample holder is tilted to a third angle for STEM imaging. Preferably, the face of the sample to be viewed is perpendicular to the SEM column In optional step 432, the sample is imaged using TEM/STEM. The grid could also be transferred to a separate TEM for analysis as is known in the prior art.

Figure 4B:
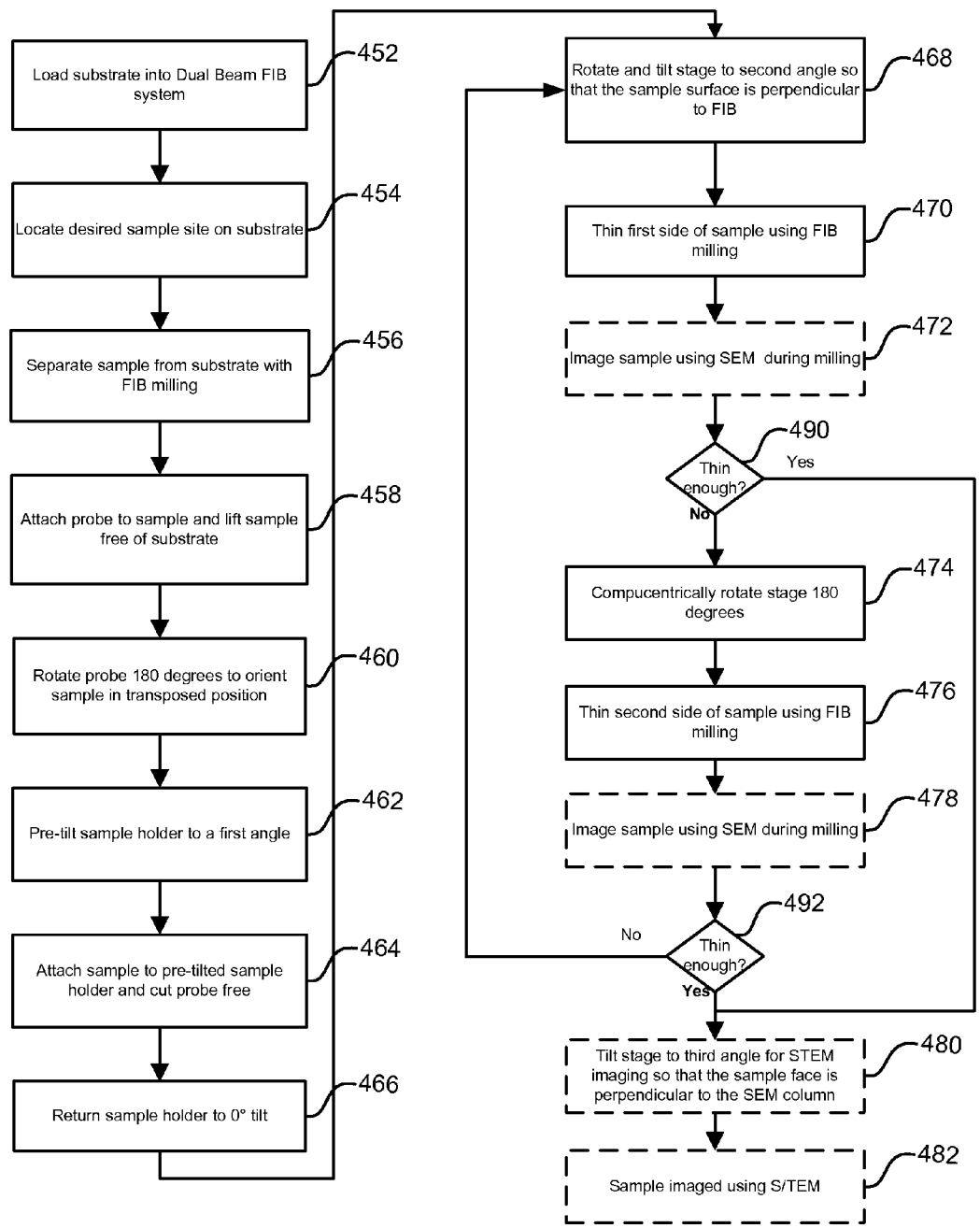
FIG. 4B is a flowchart showing the steps of creating and imaging of a backside thinned cross-sectional sample according to a preferred embodiment of the present invention in which the lift-out probe is at any angle relative to the sample.

In some embodiments of the present invention, however, it will be desirable to use a lift-out probe that is oriented at an angle other than 45 degrees relative to the sample surface. For example, in some commercially available dual beam systems the lift-out probe is oriented at an angle of approximately 50 degrees. FIG. 4B is a flowchart showing the steps of creating and imaging of a backside thinned cross-sectional sample according to some embodiments of the present invention where the lift-out probe needle is oriented at angles other than 45 degrees relative to the sample surface. Various steps in the process are shown in FIGS. 5A-5G and FIGS. 6A-6B.

In step 452, a substrate such as a semiconductor wafer or portion thereof is loaded into a Dual Beam FIB-SEM system having both a FIB column and a SEM column A typical dual-beam configuration is an electron column having a vertical axis with an ion column having an axis tilted with respect to the vertical (usually at a tilt of approximately 52 degrees). The substrate can be auto-loaded, as is well known in the art, although the substrate can also be loaded manually. The steps of this process are preferably performed within the dual-beam system.

In step 454, the location of a sample (containing a feature of interest) to be extracted from a substrate is determined For example, the substrate may be a semiconductor wafer or portion thereof and the portion to be extracted may include a portion of an integrated circuit that is to be observed using the TEM. The dual beam system's imaging capabilities can be used to visually select the area which contains the feature of interest. The system's navigation capabilities can also be used to select the area of interest by providing coordinates to the system which are mapped to the substrate and having the system navigate to those coordinates.

In step 456, the sample is separated from the substrate by milling with a focused ion beam as described above and shown in FIGS. 2-3. Next, in step 458, a lift-out probe tip is attached to the sample by FIB-induced chemical vapor deposition and the sample is lifted free of the substrate as shown in FIG. 5A. The probe can be attached to the sample, for example, by static electricity, FIB deposition, or an adhesive. In this embodiment, the probe can be oriented at any angle relative to the surface of the sample. Steps 456 and 458 are preferably carried out with the FIB-SEM sample stage at a tilt of zero degrees (so that the sample stage plane is perpendicular to the vertical).

In step 460, the lift-out probe needle is rotated 180 degrees, changing the orientation of the sample from a horizontal position shown in FIG. 5B to a transposed position shown in FIG. 5C. In this embodiment, for example, with the lift-out probe attached when oriented at 50 degrees relative to the sample (horizontal plane), rotating the lift-out needle 180 degrees about its axis, will transpose the sample surface into a vertical position of 80 degrees relative to the horizontal plane.

Figure 6A:
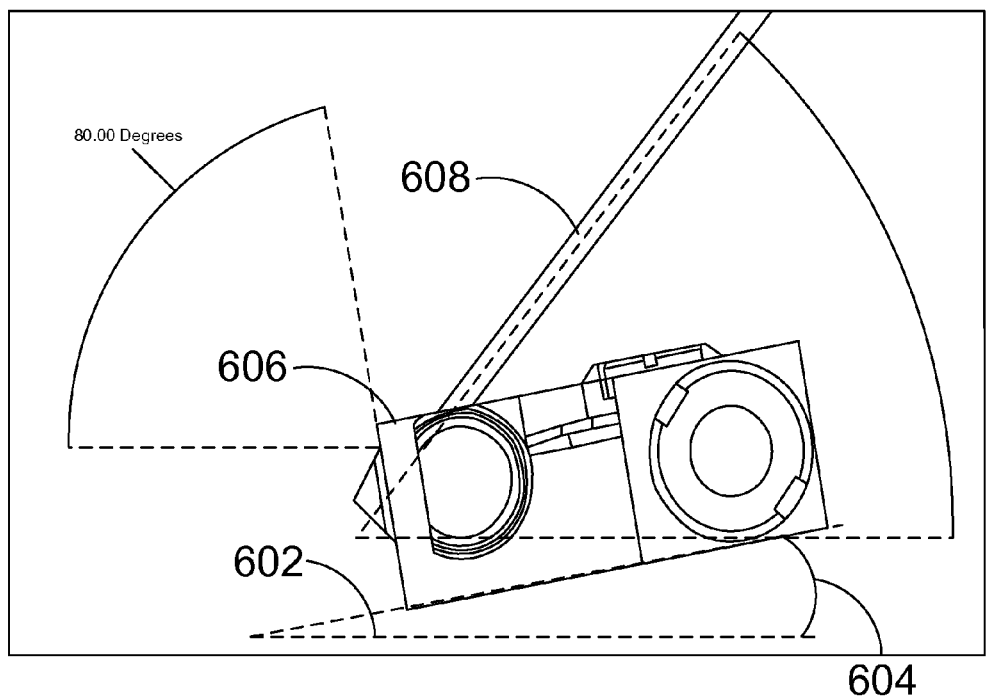
FIG. 6A is an example mock-up side view of a sample to be attached to a holder mounted on a stage which is pre-tilted.
Figure 6B:
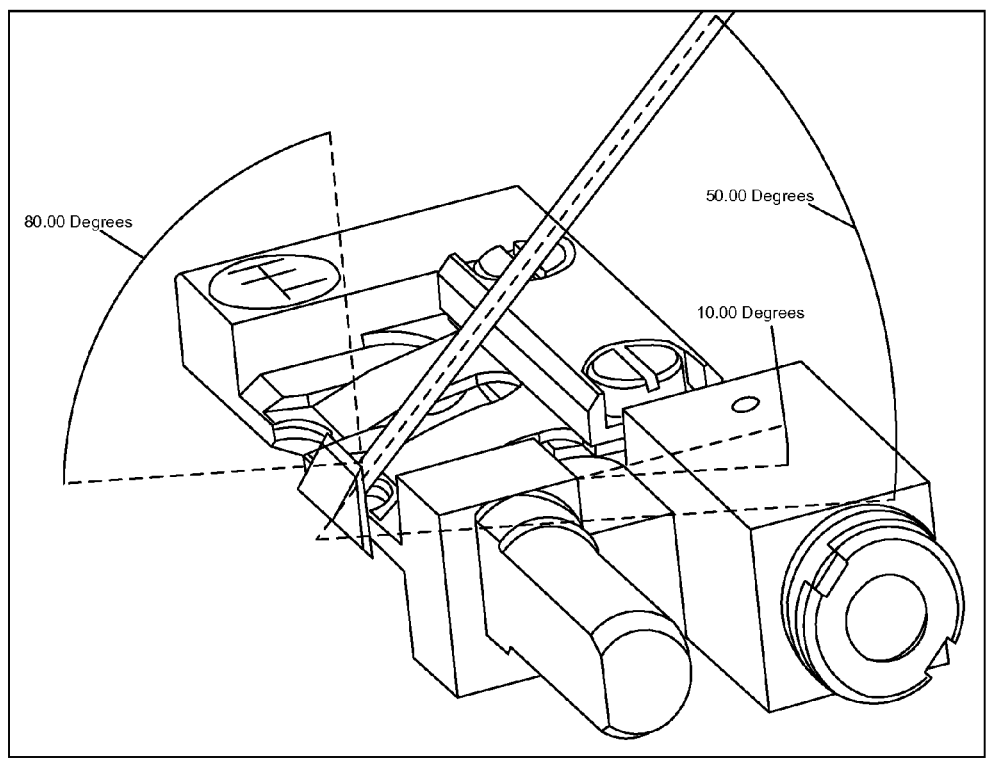
FIG. 6B is an example mock-up perspective view of a sample to be attached to a holder mounted on a stage which is pre-tilted.

In step 462, the TEM sample holder is preferably pre-tilted to a first angle 604 relative to the horizontal plane 602 by tilting the sample holder as shown in FIGS. 6A-6B. The TEM sample holder 606 is preferably mounted vertically onto a stage so that the vertical axis of the sample holder is perpendicular to the plane of the sample stage surface. The sample holder 606 is preferably capable of tilting a sample from 0 to 100 degrees relative to the stage surface. In some embodiments, the sample holder 606 is preferably capable of tilting a sample from 0 up to 180 degrees relative to the stage surface. Further, the stage (not shown) is preferably capable of moving in the X, Y, and Z directions and will preferably comprise a rotating and tilting stage having a maximum tilt of 90 degrees. In some embodiment, the tilting stage will preferably have a maximum tilt of more than 90 degrees. In this embodiment, for example in FIGS. 6A-6B, the sample holder has been pre-tilted to an angle of 10 degrees 604, which in turn tilts the sample to an angle of 10 degrees (relative to the sample holder plane with the stage tilt at zero degrees).

In step 464, the rotated sample is attached to the tilted grid as shown in FIGS. 6A-6B and then the attached probe 608 is cut free. The top surface of the sample is perpendicular to the grid. Because the sample holder is pre-tilted to a first angle and because the sample top surface remains in its original orientation, the top surface of the mounted sample will be located at the same first angle with respect to the TEM sample holder plane.

In step 466, the sample holder is returned to zero degree tilt as shown in FIG. 5E. In step 468, shown in FIG. 5F, the stage is preferably rotated and then tilted to a second angle such that the top surface of the mounted sample is preferably oriented substantially perpendicular to the orientation of the FIB column, preferably having the backside surface exposed to the FIB column. The second angle of tilt preferably allows for an orthogonal face surface to be formed.

In step 470, the first side of sample is thinned using FIB milling as shown in FIG. 5F. Milling from the backside is preferred and minimizes or prevents curtaining. In step 472, the sample is preferably imaged using an SEM during the milling of the sample.

Once the first side of the sample is thinned, in step 474 the sample is preferably compucentrically rotated 180 degrees so that the second side of the sample can be thinned. The sample holder is tilted to a vertical position perpendicular to the stage and the stage is then rotated 180 degrees. Other methods of rotation and re-orientation of the sample are possible in which the second side of the sample is positioned for thinning Next, the stage is tilted to the second angle such that the top surface of the mounted sample is preferably oriented substantially perpendicular to the orientation of the FIB column, preferably having the backside surface exposed to the FIB column as shown in FIG. 5G. The second angle of tilt preferably allows for an orthogonal face surface to be formed.

In step 476, the second side of the sample is thinned using FIB milling as shown in FIG. 5G. Milling from the backside is preferred and minimizes or prevents curtaining. In step 478, the sample is preferably imaged using an SEM during the milling of the sample.

Steps 468 through 478 can be repeated as needed to thin the sample to desired thickness or until a feature of the sample is visible or available for imaging. In decision block 490, if the sample is thinned to the desired thickness or feature and no further thinning is required, then the process proceeds to optional step 480. If the sample requires additional thinning, the process returns to step 474 and the second side of the sample is subsequently thinned. In decision block 492, if the sample is thinned to the desired thickness or feature and no further thinning is required, then the process proceeds to optional step 480. If the sample requires additional thinning, then the process returns to step 468 and the first side of the sample is subsequently thinned again.

Once thinning of both sides of the sample is completed, the remaining sample is sufficiently thin for viewing with transmission electron microscopy. Optionally in step 480, the sample is tilted to a third angle for STEM imaging. Preferably, the face of the sample to be viewed is perpendicular to the SEM column In optional step 482, the sample is imaged using TEM/STEM.

In some embodiments of the present invention, the pre-tilt process described above can be used in preparing samples other than back-thinned samples. For example, U.S. Pat. No. 7,423,263 to Hong et al. for "Planar View Sample Preparation," which is assigned to the assignee of the present invention and is hereby incorporated by reference, describes preparing a planar view sample using a lift-out probe needle at an angle of 45 degrees relative to the top surface of the sample, then rotating the needle about its axis 180 degrees, thus transposing the sample orientation from horizontal to vertical. Where a lift-out probe at an angle other than 45 degrees is used, the pre-tilting process described above can be used to properly orient the sample and grid for planar sample thinning and viewing.

Figure 7:
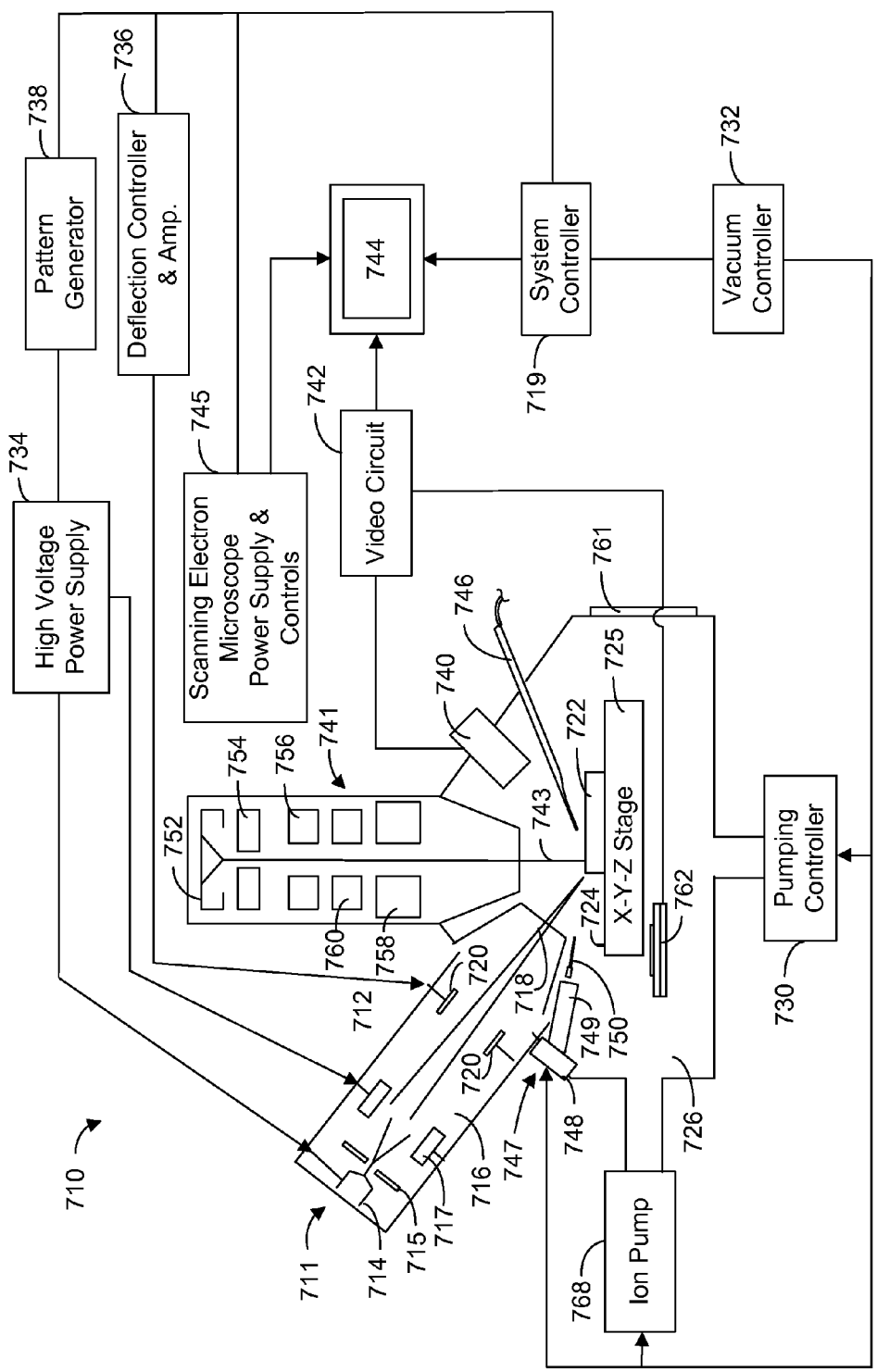
FIG. 7 is a diagram showing a typical dual beam system suitable for practicing the present invention.

In some embodiments of the present invention, a top down cross-sectional view sample is created and imaged according to the invention. In these embodiments, the top surface of the sample is perpendicular and facing the FIB column as each side is thinned allowing the SEM column to have an unobstructed access to the sample, thus viewing of the sample during the milling operation is possible. The compucentric 180 degree rotation step described above can be used after the first side of the sample is thinned, to also allow viewing of the second side milling using a vertically mounted SEM column FIG. 7 shows a typical dual beam system 710 suitable for practicing the present invention, with a vertically mounted SEM column and a focused ion beam (FIB) column mounted at an angle of approximately 52 degrees from the vertical. Suitable dual beam systems are commercially available, for example, from FEI Company, Hillsboro, Oregon, the assignee of the present application. While an example of suitable hardware is provided below, the invention is not limited to being implemented in any particular type of hardware.

A scanning electron microscope 741, along with power supply and control unit 745, is provided with the dual beam system 710. An electron beam 743 is emitted from a cathode 752 by applying voltage between cathode 752 and an anode 754. Electron beam 743 is focused to a fine spot by means of a condensing lens 756 and an objective lens 758. Electron beam 743 is scanned two-dimensionally on the specimen by means of a deflection coil 760. Operation of condensing lens 756, objective lens 758, and deflection coil 760 is controlled by power supply and control unit 745.

Electron beam 743 can be focused onto substrate 722, which is on movable X-Y stage 725 within lower chamber 726. When the electrons in the electron beam strike substrate 722, secondary electrons are emitted. These secondary electrons are detected by secondary electron detector 740 as discussed below. STEM detector 762, located beneath the TEM sample holder 724 and the stage 725, can collect electrons that are transmitted through the sample mounted on the TEM sample holder as discussed above.

Dual beam system 710 also includes focused ion beam (FIB) system 711 which comprises an evacuated chamber having an upper neck portion 712 within which are located an ion source 714 and a focusing column 716 including extractor electrodes and an electrostatic optical system. The axis of focusing column 716 is tilted 52 degrees from the axis of the electron column. The ion column 712 includes an ion source 714, an extraction electrode 715, a focusing element 717, deflection elements 720, and a focused ion beam 718. Ion beam 718 passes from ion source 714 through column 716 and between electrostatic deflection means schematically indicated at 720 toward substrate 722, which comprises, for example, a semiconductor device positioned on movable X-Y stage 725 within lower chamber 726.

Stage 725 can also support one or more TEM sample holders 724 so that a sample can be extracted from the semiconductor device and moved to a TEM sample holder. Stage 725 can preferably move in a horizontal plane (X and Y axes) and vertically (Z axis). Stage 725 can also tilt and rotate about the Z axis. In some embodiments, a separate TEM sample stage (not shown) can be used. Such a TEM sample stage will also preferably be moveable in the X, Y, and Z axes. A door 761 is opened for inserting substrate 722 onto X-Y stage 725 and also for servicing an internal gas supply reservoir, if one is used. The door is interlocked so that it cannot be opened if the system is under vacuum.

An ion pump 768 is employed for evacuating neck portion 712. The chamber 726 is evacuated with turbomolecular and mechanical pumping system 730 under the control of vacuum controller 732. The vacuum system provides within chamber 726 a vacuum of between approximately $1\times10^{-7}$ Torr ($1.3\times10^{-7}$ mbar) and $5\times10^{-4}$ Torr ($6\times10^{-4}$ mbar.) If an etch assisting, an etch retarding gas, or a deposition precursor gas is used, the chamber background pressure may rise, typically to about $1\times10^{-5}$ Torr ($1.3\times10^{-5}$ mbar).

The high voltage power supply provides an appropriate acceleration voltage to electrodes in ion beam focusing column focusing 716 for energizing and focusing ion beam 718. When it strikes substrate 722, material is sputtered, that is physically ejected, from the sample. Alternatively, ion beam 718 can decompose a precursor gas to deposit a material.

High voltage power supply 734 is connected to liquid metal ion source 714 as well as to appropriate electrodes in ion beam focusing column 716 for forming an approximately 1 keV to 60 keV ion beam 718 and directing the same toward a sample. Deflection controller and amplifier 736, operated in accordance with a prescribed pattern provided by pattern generator 738, is coupled to deflection plates 720 whereby ion beam 718 may be controlled manually or automatically to trace out a corresponding pattern on the upper surface of substrate 722. In some systems the deflection plates are placed before the final lens, as is well known in the art. Beam blanking electrodes (not shown) within ion beam focusing column 716 cause ion beam 718 to impact onto blanking aperture (not shown) instead of substrate 722 when a blanking controller (not shown) applies a blanking voltage to the blanking electrode.

The liquid metal ion source 714 typically provides a metal ion beam of gallium. The source typically is capable of being focused into a sub one-tenth micrometer wide beam at substrate 722 for either modifying the substrate 722 by ion milling, enhanced etch, material deposition, or for the purpose of imaging the substrate 722.

A charged particle detector 740, such as an Everhart Thornley or multi-channel plate, used for detecting secondary ion or electron emission is connected to a video circuit 742 that supplies drive signals to video monitor 744 and receiving deflection signals from controller 719. The location of charged particle detector 740 within lower chamber 726 can vary in different embodiments. For example, a charged particle detector 740 can be coaxial with the ion beam and include a hole for allowing the ion beam to pass. In other embodiments, secondary particles can be collected through a final lens and then diverted off axis for collection.

A micromanipulator 747, such as the AutoProbe 200™ from Omniprobe, Inc., Dallas, Tex., or the Model MM3A from Kleindiek Nanotechnik, Reutlingen, Germany, can precisely move objects within the vacuum chamber. Micromanipulator 747 may comprise precision electric motors 748 positioned outside the vacuum chamber to provide X, Y, Z, and theta control of a portion 749 positioned within the vacuum chamber. The micromanipulator 747 can be fitted with different end effectors for manipulating small objects. In the embodiments described herein, the end effector is a thin probe 650.

A gas delivery system 746 extends into lower chamber 726 for introducing and directing a gaseous vapor toward substrate 722. U.S. Pat. No. 5,851,413 to Casella et al. for "Gas Delivery Systems for Particle Beam Processing," assigned to the assignee of the present invention, describes a suitable gas delivery system 746. Another gas delivery system is described in U.S. Pat. No. 5,435,850 to Rasmussen for a "Gas Injection System," also assigned to the assignee of the present invention. For example, iodine can be delivered to enhance etching, or a metal organic compound can be delivered to deposit a metal.

A system controller 719 controls the operations of the various parts of dual beam system 710. Through system controller 719, a user can cause ion beam 718 or electron beam 743 to be scanned in a desired manner through commands entered into a conventional user interface (not shown). Alternatively, system controller 719 may control dual beam system 710 in accordance with programmed instructions. In some embodiments, dual beam system 710 incorporates image recognition software, such as software commercially available from Cognex Corporation, Natick, Mass., to automatically identify regions of interest, and then the system can manually or automatically extract samples in accordance with the invention. For example, the system could automatically locate similar features on semiconductor wafers including multiple devices, and take samples of those features on different (or the same) devices.

The invention described above has broad applicability and can provide many benefits as described and shown in the examples above. The embodiments will vary greatly depending upon the specific application, and not every embodiment will provide all of the benefits and meet all of the objectives that are achievable by the invention. For example, in a preferred embodiment TEM samples are created using a gallium liquid metal ion source to produce a beam of gallium ions focused to a sub-micrometer spot. Such focused ion beam systems are commercially available, for example, from FEI Company, the assignee of the present application. However, even though much of the previous description is directed toward the use of FIB milling, the milling beam used to process the desired TEM samples could comprise, for example, an electron beam, a laser beam, or a focused or shaped ion beam, for example, from a liquid metal ion source or a plasma ion source, or any other charged particle beam. Further, although much of the previous description is directed at semiconductor wafers, the invention could be applied to any suitable substrate or surface.

Skilled persons will recognize that the terms "horizontal" and "vertical" are defined in relation to a typical system in which the plane of an untilted sample stage is horizontal. The absolute angle of "horizontal" and "vertical" could change depending on the orientation of the system. It will also be understood that forming a vertical surface may entail orienting the focused ion beam column at a slight angle from the desired vertical surface to compensate from the Gaussian profile of the focused ion beam. Therefore references in the application and claims to milling normal to the sample surface include milling operations at a slight angle to the sample surface.

Some embodiments of the invention include a method for preparing a sample for imaging, the sample being formed from a work piece and having a top side and a back side, the sample being prepared for imaging by thinning the sample using an ion beam directed from the back side, comprising:

attaching a probe to the top side of the sample, the probe making a first angle with the top surface of the sample;

extracting the sample from the work piece;

rotating the probe by 180 degrees to change the orientation of the top surface of the sample from a horizontal position to transposed position;

attaching the sample to a tiltable sample holder so that the top surface of the sample is perpendicular to the sample holder plane;

tilting the sample holder so that the plane of the sample holder is oriented at 90 degrees relative to the sample stage, with the back side of the sample facing away from the sample stage;

tilting the sample stage such that the top surface of the sample is oriented approximately perpendicular to the optical axis of a FIB column, with the back side of the sample facing the FIB column;

thinning the sample from a first side of the sample by milling the sample from the back side using the ion beam;

rotating the stage by 180 degrees; and thinning the sample from a second side of the sample by milling the sample from the backside using the ion beam, said thinning the second side from the second side producing a surface parallel to the surface produced by thinning the sample from the first side.

In some embodiments, rotating the probe by 180 degrees includes rotating the probe by 180 degrees to change the orientation of the top surface of the freed sample from a horizontal position to a transposed position in which the top surface of the sample is vertical.

In some embodiments, rotating the probe by 180 degrees includes rotating the probe by 180 degrees to change the orientation of the top surface of the freed sample from a horizontal position to a transposed position in which the top surface is tilted relative to a vertical plane; and attaching the sample to a tiltable sample holder so that the top surface of the sample is perpendicular to the sample holder plane includes tilting the sample holder so that the top surface of the probe is oriented normal to the plane of the sample holder prior to attachment of the sample.

In some embodiments, attaching a probe to the top side of the sample comprises attaching a probe to the top side of a wedge-shaped sample.

In some embodiments, attaching the probe comprises attaching the probe before the wedge-shaped sample is completely freed from the work piece.

In some embodiments, attaching a probe to the top side of the sample comprises attaching a probe to the top side of a lamella.

In some embodiments, tilting the sample stage such that the top surface of the sample is oriented approximately perpendicular to the optical axis of the FIB column comprises tilting the sample stage such that the top surface of the sample is oriented approximately within 10 degrees of the FIB column.

In some embodiments, rotating the stage by 180 degrees comprises compucentrically rotating the stage by 180 degrees.

Some embodiments of the invention include a method for preparing a sample for imaging, the sample being extracted from a work piece and thinned by directing an ion beam to the sample from the backside of the sample, comprising:
    attaching a probe to the sample;
    separating the sample from the work piece;
    rotating the probe;
    attaching the sample to a tiltable sample holder on a stage that can tilt and rotate;
    detaching the probe from the sample;
    tiling the sample holder and the stage to present the back side of the sample to the focused ion beam for milling;
    milling one side of the sample from the back side of the sample to thin the sample; and
    milling the other side of the sample from the back side of the sample to thin the sample, wherein from the time that the sample is extracted from the work piece, it is attached to the probe only a single time and to the sample holder only a single time.

In some embodiments, all steps are performed within a vacuum chamber and are performed without venting the vacuum chamber.

In some embodiments, attaching a probe to the sample is performed before the sample is separated from the work piece.

In some embodiments, tiling the sample holder and the stage to present the back side of the sample to the focused ion beam for milling comprises: tiling the sample holder so that the plane of the sample holder is perpendicular to the plane of the stage; and tilting the stage so that the plane of the stage surface is perpendicular to the ion beam.

In some embodiments, rotating the probe comprises rotating the probe 180 degrees.

In some embodiments, attaching a probe to the sample comprises attaching the probe at an angle of 45 degree to the sample top surface.

In some embodiments, attaching a probe to the sample comprises attaching the probe at an angle of 50 degree to the sample top surface; and attaching the sample to a tiltable sample holder includes tilting the sample holder so that the plane of the sample holder forms an angle of 10 degrees from the horizontal, thereby providing an angle of 90 degrees between the front sample surface and the sample holder.

In some embodiments, attaching a probe to the sample comprises attached a probe at a first angle to the sample top surface; and attaching the sample to a tiltable sample holder on a stage that can tilt and rotate includes tilting the sample holder to a second angle from the horizontal, the second angle being twice the difference between the first angle and 45 degrees.

In some embodiments, the method further comprises orienting the sample holder and sample stage so that a thinned sample surface is normal to the optical axis of an electron beam column; directing an electron beam toward the sample; and detecting electrons that are transmitted through the sample.

In some embodiments, milling one side of the sample includes examining the results of the milling operation using an electron beam to determine when to stop thinning the sample.

In some embodiments, tiling the sample holder and the stage to present the back side of the sample to the focused ion beam for milling includes tiling the sample holder and the stage so that a normal to the top surface of the sample is oriented to within 10 degrees the ion beam axis.

In some embodiments, the stage is rotated between milling the one side and milling the other side of the sample.

In some embodiments, rotating the stage by 180 degrees comprises compucentrically rotating the stage by 180 degrees.

In some embodiments, attaching a probe to the sample comprises attaching the probe to the sample using ion beam deposition and in which detaching the probe from the sample comprises ion beam milling.

In some embodiments, tiling the sample holder and the stage to present the back side of the sample to the focused ion beam for milling includes tiling the sample holder and the stage so that the ion beam forms a surface that is oriented substantially normal to the front surface of the sample.

In some embodiments, the ion beam forms an angle of less than 10 degrees with the front surface of the sample.

In some embodiments, the deviation of the ion beam angle from the normal to the sample front surface is such that a substantially vertical surface is formed on both sides of the sample to produce a sample having two parallel surfaces to produce a substantially uniform thickness.

Although the present invention and its advantages have been described in detail, it should be understood that various changes, substitutions and alterations can be made to the embodiments described herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A method for preparing a cross-sectional view sample for imaging, the sample being formed from a work piece and having a top side and a back side, the sample being prepared for imaging by thinning the sample using an ion beam directed from the back side, comprising:

attaching a probe to the top side of the sample, the probe making a first angle with the top surface of the sample;

extracting the sample from the work piece;

rotating the probe by 180 degrees to change the orientation of the top surface of the sample from a horizontal position to transposed position;

attaching the sample to an independently tiltable sample holder so that the top surface of the sample is perpendicular to the sample holder plane;

tilting the sample holder so that the plane of the sample holder is oriented at 90 degrees relative to a sample stage, with the back side of the sample facing away from the sample stage;

tilting the sample stage such that the top surface of the sample is oriented approximately perpendicular to the optical axis of a FIB column, with the back side of the sample facing the FIB column;

thinning the sample from a first side of the sample by milling the sample from the back side using the ion beam;

rotating the stage by 180 degrees; and thinning the sample from a second side of the sample by milling the sample from the backside using the ion beam, said thinning the second side from the second side producing a surface parallel to the surface produced by thinning the sample from the first side.

2. The method of claim 1 in which rotating the probe by 180 degrees includes rotating the probe by 180 degrees to change the orientation of the top surface of the freed sample from a horizontal position to a transposed position in which the top surface of the sample is vertical.

3. The method of claim 1 in which:

rotating the probe by 180 degrees includes rotating the probe by 180 degrees to change the orientation of the top surface of the freed sample from a horizontal position to a transposed position in which the top surface is tilted relative to a vertical plane; and attaching the sample to a tiltable sample holder so that the top surface of the sample is perpendicular to the sample holder plane includes tilting the sample holder so that the top surface of the probe is oriented normal to the plane of the sample holder prior to attachment of the sample.

4. The method of claim 1 in which attaching a probe to the top side of the sample comprises attaching a probe to the top side of a wedge-shaped sample.

5. The method of claim 4 in which attaching the probe comprises attaching the probe before the wedge-shaped sample is completely freed from the work piece.

6. The method of claim 1 in which attaching a probe to the top side of the sample comprises attaching a probe to the top side of a lamella.

7. The method of claim 1 in which tilting the sample stage such that the top surface of the sample is oriented approximately perpendicular to the optical axis of the FIB column comprises tilting the sample stage such that the top surface of the sample is oriented approximately within 10 degrees of the FIB column.

8. The method of claim 1 in which rotating the stage by 180 degrees comprises compucentrically rotating the stage by 180 degrees.

9. A method for preparing a cross-sectional view sample for imaging, the sample being extracted from a work piece and thinned by directing an ion beam to the sample from the backside of the sample, comprising:

attaching a probe to the sample;

separating the sample from the work piece;

rotating the probe;

attaching the sample to an independently tiltable sample holder on a stage that can tilt and rotate;

detaching the probe from the sample;

tilting the sample holder and the stage to present the back side of the sample to the focused ion beam for milling;

milling one side of the sample from the back side of the sample to thin the sample; and milling the other side of the sample from the back side of the sample to thin the sample, wherein from the time that the sample is extracted from the work piece, it is attached to the probe only a single time and to the sample holder only a single time.

10. The method of claim 9 in which all steps are performed within a vacuum chamber and are performed without venting the vacuum chamber.

11. The method of claim 9 in which attaching a probe to the sample is performed before the sample is separated from the work piece.

12. The method of claim 9 in which tiling the sample holder and the stage to present the back side of the sample to the focused ion beam for milling comprises:

tilting the sample holder so that the plane of the sample holder is perpendicular to the plane of the stage; and tilting the stage so that the plane of the stage surface is approximately perpendicular to the ion beam.

13. The method of claim 9 in which tiling the sample holder and the stage to present the back side of the sample to the focused ion beam for milling includes tiling the sample holder and the stage so that the ion beam forms a surface that is oriented substantially normal to the front surface of the sample.

14. The method of claim 13 in which the ion beam forms an angle of less than 10 degrees with the front surface of the sample.

15. The method of claim 9 in which rotating the probe comprises rotating the probe 180 degrees.

16. The method of claim 9 in which attaching a probe to the sample comprises attaching the probe at an angle of 45 degrees to the sample top surface.

17. The method of claim 9 in which:

attaching a probe to the sample comprises attaching the probe at an angle of 50 degrees to the sample top surface; and attaching the sample to a tiltable sample holder includes tilting the sample holder so that the plane of the sample holder forms an angle of 10 degrees from the horizontal, thereby providing an angle of 90 degrees between the front sample surface and the sample holder.

18. The method of claim 9 in which:

attaching a probe to the sample comprises attached a probe at a first angle to the sample top surface; and attaching the sample to a tiltable sample holder on a stage that can tilt and rotate includes tilting the sample holder to a second angle from the horizontal, the second angle being twice the difference between the first angle and 45 degrees.

19. The method of claim 9 in which attaching a probe to the sample includes attaching a lamella-shaped sample to the probe.

20. The method of claim 9 in which attaching a probe to the sample includes attaching a wedge-shaped sample to the probe.

21. The method of claim 9 further comprising:

orienting the sample holder and sample stage so that a thinned sample surface is normal to the optical axis of an electron beam column;

directing an electron beam toward the sample; and
detecting electrons that are transmitted through the sample.

22. The method of claim 9 in which milling one side of the sample includes examining the results of the milling operation using an electron beam to determine when to stop thinning the sample.

23. The method of claim 9 in which tilting the sample holder and the stage to present the back side of the sample to the focused ion beam for milling includes tiling the sample holder and the stage so that a normal to the top surface of the sample is oriented to within 10 degrees the ion beam axis.

24. The method of claim 9 further comprising rotating the stage 180 degrees between milling the first side and milling the other side.

25. The method of claim 24 in which rotating the stage by 180 degrees comprises compucentrically rotating the stage by 180 degrees.

26. The method of claim 9 in which attaching a probe to the sample comprises attaching the probe to the sample using ion beam deposition and in which detaching the probe from the sample comprises ion beam milling.

\* \* \* \* \*

UNITED STATES PATENT AND TRADEMARK OFFICE
CERTIFICATE OF CORRECTION

PATENT NO. : 9,653,260 B2
APPLICATION NO. : 13/691270
DATED : May 16, 2017
INVENTOR(S) : Paul Keady et al.

It is certified that error appears in the above-identified patent and that said Letters Patent is hereby corrected as shown below:

1. Column 13, Line 32, please change "tiling the sample holder" to read --tilting the sample holder--

2. Column 13, Line 47, please change "In some embodiments, tiling the sample holder" to read --In some embodiments, tilting the sample holder--

3. Column 13, Line 49, please change "comprises; tiling the sample holder" to read --comprises; tilting the sample holder--

4. Column 14, Line 16, please change "In some embodiments, tiling the sample holder" to read --In some embodiments, tilting the sample holder--

5. Column 14, Line 18, please change "milling includes tiling the sample holder" to read --milling includes tilting the sample holder--

6. Column 14, Line 30, please change "In some embodiments, tiling the sample holder" to read --In some embodiments, tilting the sample holder--

7. Column 14, Line 32, please change "milling includes tiling the sample holder" to read --milling includes tilting the sample holder--

8. Claim 12, Column 16, Line 20, please change "The method of Claim 9 in which tiling the sample" to read --The method of Claim 9 in which tilting the sample--

9. Claim 13, Column 16, Line 27, please change "The method of Claim 9 in which tiling the sample" to read --The method of Claim 9 in which tilting the sample--

10. Claim 13, Column 16, Line 29, please change "milling includes tiling the" to read --milling includes tilting the--

Signed and Sealed this
Fourteenth Day of August, 2018

Andrei Iancu
*Director of the United States Patent and Trademark Office*

11. Claim 23, Column 17, Line 10, please change "milling includes tiling the" to read --milling includes tilting the--